United States Patent
Chen et al.

(10) Patent No.: US 10,273,262 B2
(45) Date of Patent: Apr. 30, 2019

(54) CRYSTALLINE FORM A OF OBETICHOLIC ACID AND PREPARATION METHOD THEREOF

(71) Applicant: CRYSTAL PHARMATECH CO., LTD., Suzhou, Jiangsu (CN)

(72) Inventors: Minhua Chen, Suzhou (CN); Yanfeng Zhang, Suzhou (CN); Xiaojuan Diao, Suzhou (CN); Xiaoyu Zhang, Suzhou (CN)

(73) Assignee: Crystal Pharmatech Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/127,750

(22) PCT Filed: Dec. 30, 2015

(86) PCT No.: PCT/CN2015/099770
§ 371 (c)(1),
(2) Date: Sep. 20, 2016

(87) PCT Pub. No.: WO2016/107575
PCT Pub. Date: Jul. 7, 2016

(65) Prior Publication Data
US 2018/0170958 A1   Jun. 21, 2018

(30) Foreign Application Priority Data
Dec. 30, 2014   (CN) .......................... 2014 1 0842176

(51) Int. Cl.
*C07J 9/00*   (2006.01)
*A61K 31/57*   (2006.01)
*A61P 1/16*   (2006.01)
*B01D 9/00*   (2006.01)

(52) U.S. Cl.
CPC ............... *C07J 9/005* (2013.01); *A61K 31/57* (2013.01); *A61P 1/16* (2018.01); *B01D 9/0018* (2013.01); *B01D 9/0054* (2013.01); *C07B 2200/13* (2013.01)

(58) Field of Classification Search
None
See application file for complete search history.

(56) References Cited

U.S. PATENT DOCUMENTS

2005/0080064 A1   4/2005   Pellicciari

FOREIGN PATENT DOCUMENTS

WO   2013192097 A1   12/2013

*Primary Examiner* — Samantha L Shterengarts
(74) *Attorney, Agent, or Firm* — VLP Law Group LLP; Kent H. Cheng

(57) ABSTRACT

The present invention relates to crystalline Form A of obeticholic acid and the preparation method thereof. The present invention provides Form A having characteristic peaks at 2theta value of 4.9°±0.2°, 5.2°±0.2°, 9.9°±0.2°. The present invention provides a novel crystalline form of obeticholic acid, which has good stability, good processability and other favorable properties, and is suitable for storage and usage as a final product. In addition, the preparation method is simple, low cost, and has great value for the future optimization and development of obeticholic acid.

11 Claims, 2 Drawing Sheets

CRYSTALLINE FORM A OF OBETICHOLIC ACID AND PREPARATION METHOD THEREOF

CROSS REFERENCE TO RELATED APPLICATIONS

This application a U.S. national phase application of PCT/CN2015/099770, filed Dec. 30, 2015, and claims priority to Chinese Patent Application No. 201410842176.1, filed on Dec. 30, 2014, all of which are herein incorporated by reference in their entireties.

TECHNICAL FIELD

The present invention relates to a novel crystalline form of obeticholic acid and a preparation method of this novel crystalline form.

BACKGROUND OF THE INVENTION

Obeticholic acid, a famesol X receptor (FXR) agonist developed by Intercept Pharmaceuticals, is used for the treatment of primary biliary cirrhosis (PBC) and nonalcoholic steatohepatitis (NASH). Obeticholic acid is currently in clinical Phase III studies, and the Phase III studies show optimistic data for treating primary biliary cirrhosis by obeticholic acid. Obeticholic acid is expected to be the first choice of a new method to treat primary biliary cirrhosis for more than 20 years in the future. Furthermore, Obeticholic acid plays an important role on improving nonalcoholic steatohepatitis. Obeticholic acid, also known as 6-ethyl-chenodeoxycholic acid, has the following structural formula:

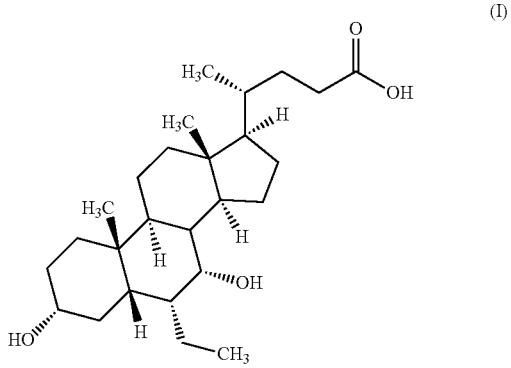

(I)

Drug polymorphism means that a drug has two or more different crystalline forms. The phenomenon of polymorphism exists widely in drugs. Different polymorphs of the same drug may have significant differences in solubility, melting point, density, stability, etc., and affect the stability, homogenicity, bioavailability, efficacy and safety of the drug. Thus, a comprehensive and systematic polymorph screening to select the most suitable crystalline form for development is one of the important researches which cannot be ignored in drug research and development.

At present, although there are reports related to crystalline forms of obeticholic acid, the reported forms were used to prepare amorphous obeticholic acid. These forms are used as intermediates to purify obeticholic acid, and they are not final products. For example, WO2013192097 reports that, Form C of obeticholic acid was prepared first, and then Form C was converted to amorphous obeticholic acid products. It was obvious that the reported Form C of obeticholic acid is an intermediate for purification and is not suitable for using as final products, since these forms have poor purity and stability, and may also have some other undesired properties; for example, Form C reported by WO2013192097 contains n-heptane.

SUMMARY OF THE INVENTION

An objective of the present invention is to provide a novel crystalline form of obeticholic acid (designated as Form A) with good stability and suitable for storage and usage as a final product.

To achieve the above purpose, the present invention employs the following technical schemes:

A crystalline Form A of obeticholic acid, the X-ray powder diffraction pattern of the crystalline form A shows characteristic peaks at 2theta values of 4.9°±0.2°, 5.2°±0.2°, and 9.9°±0.2°.

Further, the X-ray powder diffraction pattern of the crystalline Form A further shows characteristic peaks at 2theta values of 7.2°±0.2°, 7.7°±0.2°, and 10.5°±0.2°.

More further, the X-ray powder diffraction pattern of the crystalline Form A further shows characteristic peaks at 2 theta values of 6.2°±0.2°, 12.5°±0.2°, and 15.7°±0.2°.

According to a specific and preferred aspect, the X-ray powder diffraction pattern of the crystalline Form A is substantially as shown in FIG. 1.

Particularly, the X-ray powder diffraction pattern was acquired by an X-ray powder diffractometer using CuKα radiation at the temperature of 25° C.

Further, the differential scanning calorimetry analysis curve (DSC) of said crystalline Form A shows an endothermic peak when heated to 90 ~ 92° C. Preferably, the DSC thermogram of the crystalline Form A is substantially as shown in FIG. 2.

Further, the crystalline Form A is a hydrate, and the thermal gravimetric analysis (TGA) thermogram thereof shows that the water content is about 4 wt %~13 wt %. According to a specific aspect, the TGA thermogram of the crystalline Form A is substantially as shown in FIG. 3.

The present invention also provides a preparation method of the above-mentioned obeticholic acid Form A, which comprises: adding obeticholic acid powder into a crystallizing solvent to get Form A via crystallization.

According to the present invention, the preparation method includes, but not limited to, suspension slurrying, heating and cooling, evaporation, anti-solvent addition or the like. The crystallization method of suspension and slurrying usually refers to: a method by adding an excess amount of solid to a crystallizing solvent to form a suspension, and stirring at a setting temperature for a period of time, to give a crystalline form. The crystallization method of heating and cooling usually refers to: a method by adding an excess amount of solid to a crystallizing solvent and heating to a certain setting temperature, then filtering to give a saturated solution at this temperature, and setting a lower temperature and a certain cooling rate so as to precipitate out a solid and give a crystalline form from the system during the cooling process. The crystallization method of evaporation usually refers to: a method by dissolving the solid in a crystallizing solvent to give a clear solution, and slowly or rapidly evaporating the solvent to give a crystalline form. The crystallization method of adding anti-solvent usually refers to: a method by dissolving the solid in a good solvent to obtain a clear solution, and then slowly adding an anti-solvent into the clear solution to precipitate out a solid and give a crystalline form.

According to the present invention, the crystallizing solvent is selected from alcohol solvents, ketone solvents, ester solvents, aromatic hydrocarbon solvents, halogenated hydrocarbon solvents, nitrile solvents, nitroalkane solvents, cyclic ether solvents, aliphatic hydrocarbon solvents or a combination thereof.

Preferably, the crystallizing solvent is selected from ketone solvents, halogenated hydrocarbon solvents, ester solvents, aliphatic hydrocarbon solvents or a combination thereof.

More preferably, the crystallizing solvent is a combination of one or more solvents selected from ketone solvents, ester solvents and halogenated hydrocarbon solvents, and one or more solvents selected from aliphatic hydrocarbon solvents; or, the crystallizing solvent is a combination of one or more solvents selected from ester solvents. The ketone solvents include for instance methyl ethyl ketone; the aliphatic hydrocarbon solvents include for instance n-heptane; the halogenated hydrocarbon solvents include for instance chloroform; and the ester solvents include for instance ethyl acetate.

According to a specific and preferred aspect of the present invention, the crystallizing solvent is a mixed solvent of ethyl acetate and n-heptane with a volume ratio of 1:8 ~ 1:10. During crystallization, the obeticholic acid powder is added to a mixed solvent of ethyl acetate and n-heptane to obtain a suspension, and the suspension was stirred at room temperature for 2 to 3 days, then filtered, and the filter cake is dried in vacuum to give Form A.

According to another specific and preferred aspect of the present invention, the crystallizing solvent is a mixed solvent of methyl ethyl ketone and n-heptane with a volume ratio of 1:8 ~ 1:10. During crystallization process, the obeticholic acid powder is added to the mixed solvent of methyl ethyl ketone and n-heptane to obtain a suspension, and the suspension is heated to 45° C.-55° C. and stirred for 1-2 hours, then filtered to obtain a clear solution, and the clear solution is slowly cooled to 5° C. or below 5° C. to precipitate a large amount of solid during cooling process, centrifuged to obtain a solid of the lower layer which is dried under vacuum to give Form A.

According to still a specific and preferred aspect of the present invention, the solvent is a mixed solvent of chloroform and n-heptane with a volume ratio of 1:1 ~1:3. During crystallizing process, the obeticholic acid powder is added into chloroform and then filtered to obtain a clear solution, and the solution is placed on a magnetic stirrer at room temperature, and n-heptane is added dropwise with stirring to obtain a suspension, then keep stirring until a large amount of solid precipitates, and the suspension is centrifuged to obtain a solid of the lower layer which is dried in vacuum to give Form A.

Form A of the present invention has excellent stability and high purity, and is suitable as the final product for storage and usage. Specifically, Form A can be used for prevention or treatment of biliary cirrhosis (PBC) and nonalcoholic steatohepatitis (NASH) and other diseases.

The present invention also provides a pharmaceutical composition comprising the above-mentioned Form A of obeticholic acid of the present invention and pharmaceutically acceptable carriers.

Further, the pharmaceutical composition is used for the prevention or treatment of biliary cirrhosis (PBC) and non-alcoholic steatohepatitis (NASH) and other diseases.

In the pharmaceutical composition, a therapeutically effective amount of obeticholic acid Form A is added. The pharmaceutical composition can be made into various dosage forms by using the well-known methods in the field of preparations, without particular limit.

Due to the implement of the above mentioned technical schemes, the present invention has the following advantages over the prior art:

The present invention provides a novel crystalline form of obeticholic acid with good stability and suitable for storage and usage as a final product. Compared with the existing amorphous products and Form C of patent WO2013192097, this crystalline product has better stability, and can well avoid the occurrence of crystal transition during the drug storage and development, and thus avoid changing of bioavailability and efficacy.

Form A of the present invention can be prepared by several preparation methods, is easy to prepare, has no or minimum solvent residue, and the process is controllable and suitable for industrial production.

DETAILED DESCRIPTION OF THE INVENTION

The present invention will be further explained by the specific embodiments, but are not intended to limit the scope of the present invention. The skilled in the art can make improvements to the preparation methods and the used instruments within the scope of the claims, and those improvements should be considered as falling into the scope of the present invention. Accordingly, the protective scope of the present invention patent should be defined by the appended claims.

In the following embodiments, the experimental methods were implemented generally in accordance with conventional conditions or conditions recommended by the manufacturers; the obeticholic acid powder was prepared by the known methods, for example, prepared by the method disclosed in patent WO2013192097.

The abbreviations used in the invention are explained as follows:

XRPD: X-ray Powder Diffraction
DSC: Differential Scanning Calorimetry
TGA: Thermal Gravimetric Analysis X-ray powder diffraction pattern in the present invention was acquired by a Panalytical Empyrean X-ray powder diffractometer. The parameters of the X-ray powder diffraction method of the present invention were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree The pattern of differential scanning calorimetry (DSC) in the present invention was acquired by a TA Q200. The parameters of the differential scanning calorimetry (DSC) method of the present invention were as follow:

Heating rate: 10° C./min
Purge gas: nitrogen.

The pattern of thermal gravimetric analysis (TGA) in the present invention was acquired by a TA Q5000. The parameters of the thermal gravimetric analysis (TGA) method of the present invention were as follow:

Heating rate: 10° C./min;
Purge gas: nitrogen.

EXAMPLE 1

Preparation Method of Crystalline Form A of Obeticholic Acid:

216.3 mg of obeticholic acid powder was added into 5.0 mL of a mixed solvent of ethyl acetate and n-heptane with a volume ratio of 1:9 to obtain a suspension. The suspension was stirred at room temperature for 48 hours, filtered, and the filter cake was dried in a vacuum drying oven at 25° C. overnight, and tested to be crystalline Form A.

Figure 2:
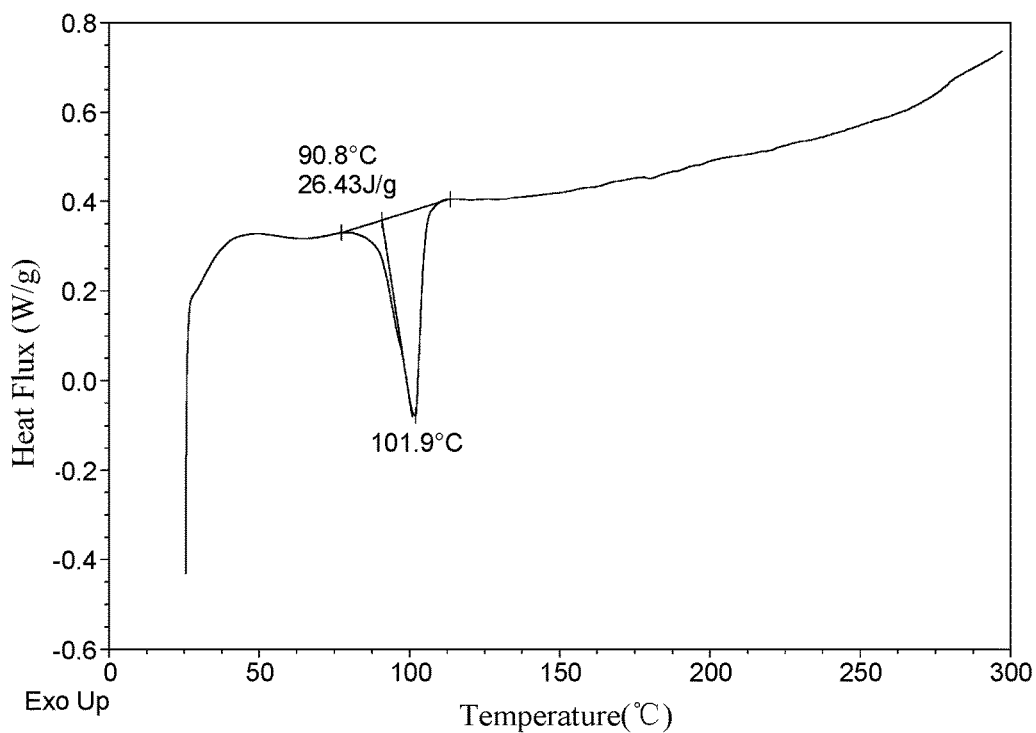
FIG. 2 shows a DSC thermogram of crystalline Form A of obeticholic acid.
Figure 3:
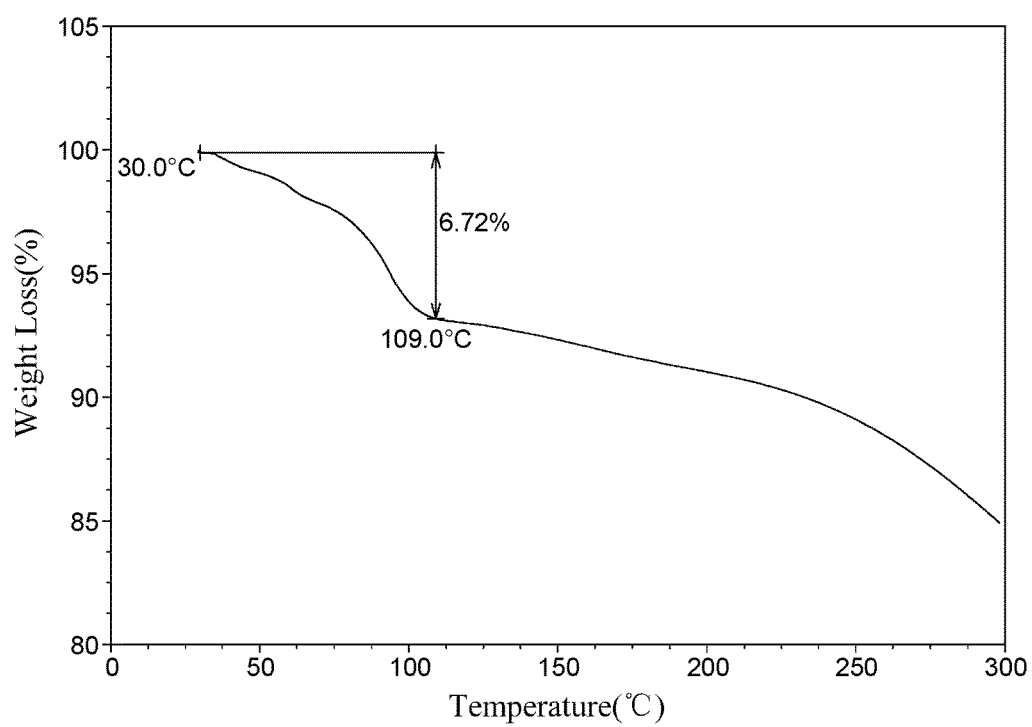
FIG. 3 shows a TGA thermogram of crystalline Form A of obeticholic acid.

The XRPD data of the crystalline Form A produced in this example is listed in Table 1. The XRPD pattern is displayed in FIG. 1, the DSC thermogram plot is displayed in FIG. 2, and the TGA thermogram plot is displayed in FIG. 3.

In addition, the purity of obeticholic acid Form A measured by evaporative light scattering method is 99.54%.

Figure 1:
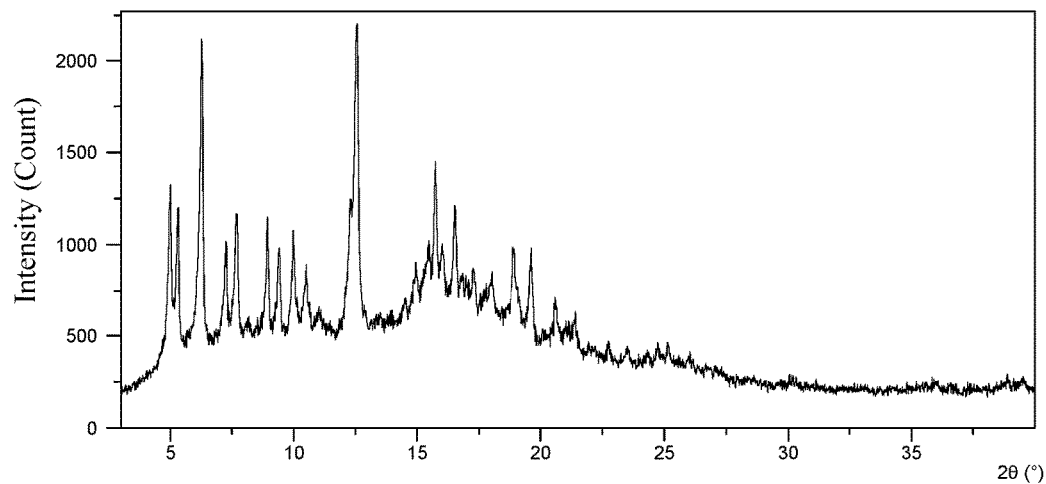
FIG. 1 shows an XRPD pattern of crystalline Form A of obeticholic acid.

Form A after storage under 5° C. for 90 days was analyzed by XRPD, and the XRPD pattern was substantially the same as FIG. 1.

TABLE 1

| 2 theta | d spacing | Relative intensity % |
|---------|-----------|----------------------|
| 4.95 | 17.87 | 55.14 |
| 5.26 | 16.79 | 51.49 |
| 6.22 | 14.20 | 100.00 |
| 7.22 | 12.24 | 39.00 |
| 7.66 | 11.54 | 49.18 |
| 8.90 | 9.93 | 42.81 |
| 9.36 | 9.44 | 38.30 |
| 9.95 | 8.89 | 43.47 |
| 10.45 | 8.46 | 30.64 |
| 10.97 | 8.06 | 20.12 |
| 12.51 | 7.08 | 99.90 |
| 14.89 | 5.95 | 32.18 |
| 15.69 | 5.65 | 62.49 |
| 15.96 | 5.55 | 37.49 |
| 16.47 | 5.38 | 49.44 |
| 17.23 | 5.15 | 30.92 |
| 17.95 | 4.94 | 28.12 |
| 18.87 | 4.70 | 36.32 |
| 19.56 | 4.54 | 31.45 |
| 20.57 | 4.32 | 21.24 |
| 21.34 | 4.16 | 15.50 |
| 22.70 | 3.92 | 7.95 |
| 23.46 | 3.79 | 6.10 |
| 24.72 | 3.60 | 6.51 |
| 25.11 | 3.55 | 7.62 |

EXAMPLE 2

Preparation Method of Crystalline Form A of Obeticholic Acid Crystalline:

39.2 mg of obeticholic acid powder was added into 5.0 mL of a mixed solvent of methyl ethyl ketone and n-heptane with a volume ratio of 1:9 to obtain a suspension. The suspension was stirred in a thermostat incubator at 50° C. for 100 min, and filtered to give a clear solution. The clear solution was slowly cooled to 5° C. at a cooling rate of 0.1° C./min. A large amount of solid precipitated during the cooling, and centrifuged to give a solid. The solid was dried in a vacuum drying oven at 25° C. overnight, and tested to be crystalline Form A.

The XRPD data of the Form A obtained from this example is listed in Table 2.

TABLE 2

| 2 theta | d spacing | Relative intensity % |
|---------|-----------|----------------------|
| 3.23 | 27.34 | 79.22 |
| 4.91 | 17.98 | 100.00 |
| 5.24 | 16.85 | 92.44 |
| 6.22 | 14.20 | 87.87 |
| 7.19 | 12.30 | 30.89 |
| 7.66 | 11.54 | 45.98 |
| 8.90 | 9.94 | 43.19 |
| 9.35 | 9.46 | 17.61 |
| 9.92 | 8.92 | 18.05 |
| 10.49 | 8.43 | 15.67 |
| 12.46 | 7.11 | 66.09 |
| 15.72 | 5.64 | 19.96 |
| 16.47 | 5.38 | 32.72 |
| 18.92 | 4.69 | 8.47 |

EXAMPLE 3

Preparation Method of Crystalline Form A of Obeticholic Acid:

9.6 mg of obeticholic acid powder was added into 0.4 mL of chloroform, and filtered to obtain a clear solution. The clear solution was stirred on a magnetic stirrer at 500 rpm at room temperature, and 0.6 mL of n-heptane was added dropwise to obtain a suspension. The suspension was stirred on a magnetic stirrer at 500 rpm for 2 days at room temperature to precipitate a large amount of solid, and centrifuged to give a solid. The solid was dried in a vacuum drying oven at 25° C. overnight, and tested to be crystalline Form A.

The XRPD data of the Form A obtained from this example is listed in Table 3.

TABLE 3

| 2 theta | d spacing | Relative intensity % |
|---------|-----------|----------------------|
| 3.09 | 28.64 | 53.73 |
| 4.92 | 17.96 | 86.44 |
| 5.24 | 16.86 | 78.78 |
| 6.22 | 14.20 | 100.00 |
| 7.21 | 12.25 | 31.06 |
| 7.66 | 11.54 | 40.10 |
| 8.90 | 9.94 | 29.26 |
| 9.37 | 9.44 | 19.04 |
| 9.93 | 8.91 | 17.08 |
| 10.51 | 8.42 | 14.71 |
| 12.50 | 7.08 | 60.41 |
| 15.72 | 5.64 | 28.09 |
| 16.48 | 5.38 | 26.45 |
| 17.95 | 4.94 | 12.8 |
| 18.97 | 4.68 | 12.44 |
| 19.58 | 4.53 | 9.40 |

EXAMPLE 4

Preparation Method of Crystalline Form A of Obeticholic Acid:

16.5 mg of obeticholic acid powder was added into 1.0 mL of ethyl acetate and filtered to give a clear solution. The clear solution was slowly evaporation at room temperature to give Form A.

The XRPD data of the Form A obtained from this example is listed in Table 4.

TABLE 4

| 2 theta | d spacing | Relative intensity % |
|---------|-----------|----------------------|
| 4.92    | 17.98     | 15.35                |
| 5.26    | 16.81     | 11.38                |
| 6.22    | 14.20     | 100.00               |
| 7.18    | 12.31     | 12.50                |
| 7.67    | 11.52     | 8.62                 |
| 8.89    | 9.95      | 12.05                |
| 9.36    | 9.44      | 12.85                |
| 9.90    | 8.93      | 14.55                |
| 10.49   | 8.44      | 6.59                 |
| 12.50   | 7.08      | 51.93                |
| 15.72   | 5.64      | 35.72                |
| 16.41   | 5.40      | 29.91                |
| 17.16   | 5.17      | 9.60                 |
| 19.00   | 4.67      | 13.12                |
| 19.56   | 4.54      | 9.80                 |
| 20.51   | 4.33      | 6.77                 |
| 24.87   | 3.58      | 1.50                 |

EXAMPLE 5

The Comparative Study of Stability of Crystalline Form A of Obeticholic Acid and Crystalline Form C in WO2013192097:

10.5 mg of crystalline Form C of obeticholic acid in patent WO2013192097 was added into 0.2 mL of a mixed solvent of ethyl acetate and n-heptane with a volume ratio of 1:9 to obtain a suspension. The suspension was stirred at 500 rpm in a thermostat at 25° C. for 24 hours, and centrifuged to give a solid which was tested by XRPD.

The results show that obeticholic acid crystalline Form C disclosed by patent WO2013192097 was transferred to crystalline Form A of the present invention in the mixed solvent of ethyl acetate and n-heptane. Thus it can be seen that, crystalline Form A is more stable than crystalline Form C in patent WO2013192097.

The examples described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

What is claimed is:

1. A crystalline Form A of Obeticholic acid, is characterized in that, the X-ray powder diffraction pattern of the crystalline Form A shows characteristic peaks at 2theta values of 4.9°±0.2°, 5.2°±0.2°, and 9.9°±0.2° using CuKα radiation.

2. The crystalline Form A according to claim 1, characterized in that, the X-ray powder diffraction pattern of the crystalline Form A further shows characteristic peaks at 2theta values of 7.2°±0.2°, 7.7°±0.2°, and 10.5°±0.2°.

3. The crystalline Form A according to claim 1, characterized in that, the X-ray powder diffraction pattern of the crystalline Form A further shows characteristic peaks at 2 theta values of 6.2°±0.2°, 12.5°±0.2°, and 15.7°±0.2°.

4. The crystalline Form A according to claim 1, characterized in that the X-ray diffraction pattern of the crystalline Form A is substantially the same as depicted in FIG. 1.

5. The crystalline Form A according to claim 1, characterized in that the differential
scanning calorimetry analysis curve of said crystalline Form A shows an endothermic peak when heated to 90-92° C.

6. The crystalline Form A according to claim 1, characterized in that said crystalline Form A is a hydrate.

7. The crystalline Form A according to claim 1, characterized in that, the water content in said crystalline Form A is 4 wt % -13 wt %.

8. A process for preparing crystalline Form A of Obeticholic acid according to claim 1, comprising: adding Obeticholic acid powder into a crystallizing solvent to affect crystallization, wherein the crystallizing solvent is a) ethyl acetate, b) a mixed solvent of ethyl acetate and n-heptane, c) a mixed solvent of methyl ethyl ketone and n-heptane, or d) a mixed solvent of chloroform and n-heptane.

9. The process according to claim 8, comprising the step of: suspending and slurrying; heating and cooling; evaporating or adding sequentially each solvent of the mixed solvent.

10. A pharmaceutical composition comprising the crystalline Form A of Obeticholic acid according to claim 1, and pharmaceutically acceptable carriers.

11. A method of treating a patient having primary biliary cirrhosis (PBC) or nonalcoholic steatohepatitis (NASH) comprising the administration of the crystalline Form A of Obeticholic acid according to claim 1 to the patient.

* * * * *